United States Patent [19]

Perilhou

[11] 4,145,610

[45] Mar. 20, 1979

[54] METHOD OF AND DEVICE FOR COMPUTED TOMOGRAPHY

[75] Inventor: Jean R. Perilhou, Bourg-la-Reine, France

[73] Assignee: U.S. Philips Corporation, New York, N.Y.

[21] Appl. No.: 785,050

[22] Filed: Apr. 6, 1977

[30] Foreign Application Priority Data

Apr. 15, 1976 [FR] France .................. 76 11153

[51] Int. Cl.² .................. A61B 6/02; G01N 23/08; G01T 1/20
[52] U.S. Cl. .................. 250/367; 250/445 T; 250/505
[58] Field of Search .................. 250/445 T, 367, 505

[56] References Cited

U.S. PATENT DOCUMENTS 3,937,965  2/1976  Vasseur .................. 250/445 T

*Primary Examiner*—Alfred E. Smith
*Assistant Examiner*—T. N. Grigsby
*Attorney, Agent, or Firm*—Thomas A. Briody; Jack E. Haken

[57] ABSTRACT

A method and apparatus for computed tomography. A radiation source and a plurality of scintillation detectors rotate about an analysis plane to measure radiation absorption therein. A like plurality of scintillator elements measure radiation from the source along lines in a reference plane which lines coincide with projections of lines connecting the detectors to the source. Fibre optics adjustably couple light from the scintillator elements to photodetectors associated with the scintillation detectors. A rotating shield alternately shields radiation from the scintillation elements and the scintillation detectors. Compensating signals for system deviations are thus produced.

7 Claims, 1 Drawing Figure

U.S. Patent        Mar. 20, 1979        4,145,610
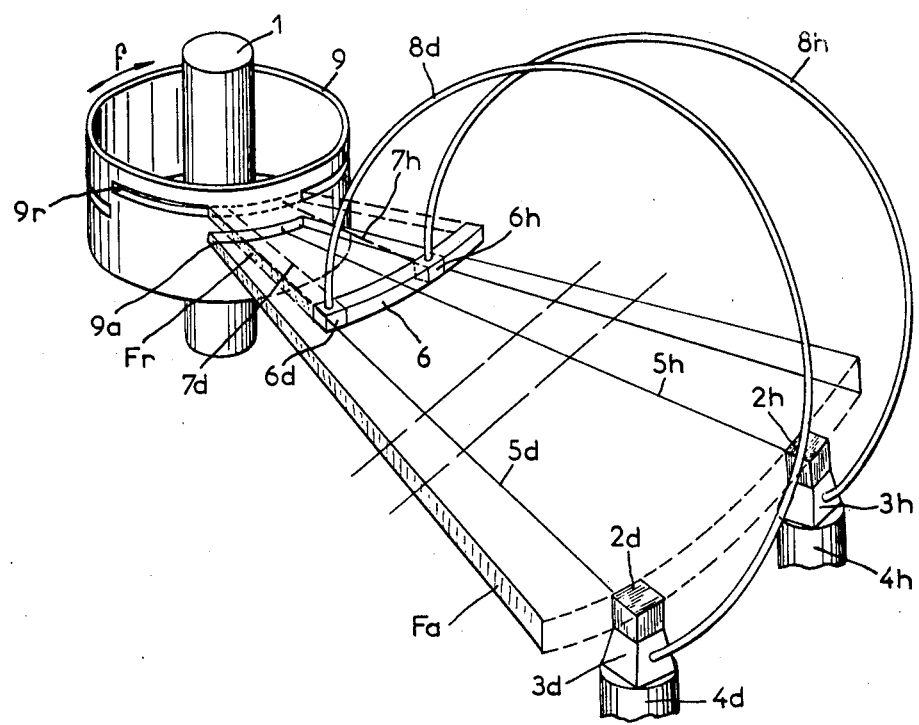

METHOD OF AND DEVICE FOR COMPUTED TOMOGRAPHY

The invention relates to a method of medical examination by radiation absorption measurement commonly known as computed tomography in which an analysis field is successively made to register with a plurality of parallel body slices of the body to be examined. Each time a plurality of elementary zones are defined at the plane of intersection of a plurality of intersecting analysis lines situated in the analysis field. The absorption measured along each of the intersecting analysis lines in the said elementary zone is mathematically processed to calculate the absorption in an elementary zone by means of measuring means which can be oriented and which comprise a radiation source and a system of n aligned scintillation measuring detectors, the positions of which relative to each other define a network of n analysis lines in the said field for each of the orientations of the measuring means. Each of the detectors is coupled, via a light conductor, to a photo-electric converter in order to supply n measuring signals I1 which are representative of the radiation absorption along the n analysis lines during each measuring series which corresponds to a given orientation of the measuring means. The said measuring signals I1 are compared with a reference signal I0 which is representative of the radiation dose of the incident radiation beam and which is supplied by a reference detector which is situated outside the analysis field. The said means also comprise means for periodically shielding the beam, to successively supply the reference signal and the n measuring signals.

The invention also relates to an apparatus for medical examination by radiation absorption measurement.

The principles of the method and of the apparatus of the kind set forth are described in the articles by A.M. Cormack, titled "Representation of a Function by the line Integrals, with some Radiological Applications", in "Journal of Applied Physics", Volume 34, No. 9 and Volume 35, No. 10, September 1963 and October 1964. The problem to be solved is formulated therein as follows:

it is assumed that the latter D denotes a two-dimensional zone with inhomogeneous absorption g, this elementary zone being traversed, along a straight line L, by a radiation beam, the radiation dose of which amounts to I0 before entering the zone. After passage through the said zone, the radiation dose then has a value I1, given by $$I1 = I0 \exp - \int_L g(s) \, ds,$$

s being a measure for the distance along the line L. If fL = ln (I0 I1), the following expression is obtained:

$$fL = \int_L f(s) \, ds.$$

The problem consists in the determination of the linear absorption coefficient g on the basis of the linear integral values fL along a plurality of intersecting lines L.

French patent specification No. 2,019,365 describes a device in which the absorption along each analysis line is derived from the radiation transfer along each analysis line and the initial dose of the incident radiation beam, measured at the point where the beam enters the body examined at each of the lines. The initial dose (I0) is obtained by means of a reference device which comprises a scintillator and an attenuator whose absorption properties correspond to those of the body to be examined, the said scintillator either being coupled, via a common optical tube, to the n photo-multipliers for n analysis lines (in that case the means comprise the said shielding means), or cooperating with a reference photomultiplier. As a result of this method of arrangement, the measurements can be correctly performed, independently of the dose fluctuations of the radiation source. The radiaton source is formed by an X-ray source in this case.

The invention has for its object to mitigate the drawbacks caused by time-dependent variations of the radiation dose of the radiation source, in this case an X-ray source as well as by variations of and differences in the properties of the detectors used, in this case preferably crystal scintillators with photomultipliers.

The method in accordance with the invention is characterized mainly in that use is made of means for measuring n signals I0 along the n reference lines which define a network configuration in a reference plane which is not the plane of the analysis field, the projection of the said network configuration in the said plane of the analysis field coinciding with the network configuration defined by the n analysis lines, the said measuring means comprising optical coupling means so that on the one hand, the signal I0 which corresponds to a reference line is supplied by the photo-electric converter which is coupled to the detector whose position determines the analysis line corresponding to the reference line, while on the other hand, the sad coupling means enable comparison of the n signals I1 and the n signals I0 which are formed in the absence of any absorbing medium in the analysis field, the means for the periodic shielding which form part of the said measuring means enabling successive measurement of the n signals I1 and the n signals I0 in any orientation of the said measuring means.

The basic advantage of the method in accordance with the invention is embodied in the fact that the causes of the instability and the lack of homogeneity in the response of the measuring means are taken into account, so that very accurate measuring results can be obtained.

The apparatus for realising the method in accordance with the invention has a very simple construction and structure and can be adapted for use of any alternative of the method in accordance with the invention. The apparatus in accordance with the invention is characterized in that a radiation source and a system of n scintillation measuring detectors are arranged in a reference plane which is not an analysis plane. A measuring device comprises a system of n scintillation detectors whose projections in the analysis plane intersect the n analysis lines defined by the mutual positions of the said source and the n measuring detectors. Each discrete scintillation detector is coupled, via an individual optical fibre, and an adjustable coupling, to a light conductor of a measuring detector in which the relevant analysis line terminates. An obturator is provided with slots for periodically shielding the radiation, the slot length and the slot movement alternately limiting the incident radiation beam to the analysis plane and the reference plane.

A preferred embodiment in accordance with the invention will be described in detail hereinafter with reference to the accompanying diagrammatic drawing.

The drawing shows the elements of the measuring means which are of essential importance in an apparatus in accordance with the invention for performing the method in accordance with the invention.

The figure shows an X-ray source 1 and two detectors 2d and 2h which are coupled to photo-electric converters 4d and 4h via light conductors 3d and 3h. This construction is known and the detectors 2d and 2h form part of a system comprising n aligned measuring detectors of the crystal scintillator type. In the plane of an analysis field the position of the said detectors relative to the X-ray source define analysis lines, for example, the lines 5d and 5h. A collimater is preferably associated with each detector.

In accordance with the invention, the measuring means comprise, in a reference plane which is not the plane of the analysis field, a system 6 comprising n discrete elements for detecting the local radiation dose by way of scintillation. Two of these elements are denoted in the figure by the references 6d and 6h. The system 6 occupies a position relative to the X-ray source so that the projections of the n discrete elements in the analysis plane intersect the n analysis lines. In other words, discrete elements define n reference lines in the reference plane (for example, the lines 7d and 7h), the projections of which coincide in the analysis plane with the n analysis lines such as, for example, the lines 5d and 5h. In accordance with the invention, each discrete element is coupled, via an optical fibre for example the fibres 8d and 8h, to the light conductor which provides an optical coupling between the corresponding detector and the associated photoelectric converter.

The means for the periodic shielding in accordance with the invention are formed by an obturator having a slot which is movable so that the X-ray beam is alternately projected in the plane of the analysis field and the reference plane, so that radiation zones Fa and fr are formed. The obturator in the figure is formed by a lead cylindrical sleeve 9 which is coaxially arranged relative to the X-ray source 1 and which is rotatable about the longitudinal axis of the source. The obturator comprises two parallel series of aligned slots, the slots 9a and 9r forming part thereof. These slots are regularly distributed over the circumference of the sleeve 9 and are preferably of the same length which is sufficient for irradiation of the n measuring detectors of the discrete elements of the system 6. The slots of one of the series have been shifted relative to those of a next series over a distance which equals half the pitch of the slots in a series. Interrupted lines in the figure denote the position of the slots of the series which includes the slot 9r when the X-ray beam is oriented towards the system 6 formed by the discrete detection elements.

It is assumed that the X-ray source is, for example, a known tube which operates at a voltage of 150 kV and which is activated in a pulsed mode during operation.

In the case of an analysis field with an opening angle of 30° the number of slots of each of the two series of slots of the obturator amounts to at the most 5, while the length of arc of each of the slots amounts to from 30° to 36°.

The rotary speed of the obturator is, for example, 3 to 5 rev/s, which results in 30 to 50 pulses per second (2 × 5 pulses per revolution). Each measuring cycle, corresponding to a given orientation in which the measuring means are oriented in the plane of the analysis field, requires two pulses, which corresponds, for the 180 cycles (one cycle per degree of rotation around a patient) required for obtaining the information required per slice of the body of the patient, to 360 pulses and a duration of from 12 to 7.5 seconds.

It has already been stated that the length of arc of the slots must be from 30° to 36. Actually, this length is necessarily larger than 30°, because the rotary movement of the obturator must be taken into account, i.e. the angular distance travelled by the said obturator during the duration of the pulse, in order to ensure that all measuring detectors or all reference detection elements receive radiation.

When the obturator rotates at a speed of three revolutions per second i.e. approximately 1000° per second, there is a play of 3° which, for a gap of 36° on both sides, permits a duration of approximately 2.7 ms ((36 - 30) / 2). Thus, a maximum is imposed as regards the duration of the pulse. When the obturator rotates at a speed of five revolutions per second, i.e. 1800° per second, the resultant maximum pulse duration will be approximately 1.6 ms. A practical length of the slots is 36° and a practical duration of the pulses is 3 ms at a rotary speed of 3 rev/s of the obturator, and 1 ms at a rotary speed of 5 rev/s of the obturator.

A practical distance between the source 1 and the measuring detectors such as, for example, the detectors 2d and 2h, amounts to, for example, 200 cm; a practical distance between the source 1 and the center of the body to be analysed then amounts to approximately 100 cm while the distance between the source 1 and the system 6 formed by the discrete detection elements amounts to approximately 50 cm.

The number of measuring detectors, and hence also the number of discrete elements of the system 6, amounts, for example, to 200. The scintillation material used to form the said measuring detectors preferably consists of sodium iodide or cesium iodide. Each measuring detector is shaped, for example, as a block proportioned 5 × 5 × 5 mm; the said block is separated from adjoining blocks by a lead collimater having a thickness of, for example, 1.5 mm and a length which is sufficient to achieve suitable collimation. Each discrete element of the system 6 may be an independent element, but the said system may alternatively be formed by a single block in which the 200 discrete elements are bounded by the mutual positions of the optical fibres whereby the said discrete elements are coupled to the light conductors which cooperate with the 200 measuring detectors. The length of the system 6 amounts to, for example, 250 cm., the thickness to 5 mm., and the height also to 5mm. The thickness of 5 mm is co-determined by the fact that the radiation absorption is then substantially 100%.

All optical fibres have the same length, i.e. a length of approximately 200 cm; the diameter of the fibres amounts to 1 mm. The coupling of the fibres to the light conductors (3d, 3h) is controllable. On one of the surfaces of the light conductors, for example, a metal control sleeve is secured which is provided with a microscrew for blocking a cap in which the end of the optical fibre is secured. The depth whereto the fibre penetrates into this control sleeve can thus be varied, so that the transmission of light to the photomultiplier can be more or less controlled.

The two measuring signals of each of the 200 successive light pulses which are produced at 6d and at 2d can be stored in a memory and can be processed at a later stage, for example, by the determination of the ratio between the two signals, one of the two signals then being used as a reference value, for example, the signal originating from 6d.

The method enables very exact measurements to be performed, even if deviations occur in the relevant photomultiplier during a measuring cycle. Individual deviations in each of the photomultipliers are now compensated for by the continuous reference to the incident beam. Thus, the light pulses which are received by the photomultiplier and which originate either from the element 6d or from the element 2d are balanced to within a few percent, so stable operation is achieved.

The radiation beam transmitted through the slots diverges more or less in a direction transverse to the analysis plane or the reference plane. The height of the slots, for example, the slot 9a, is determined by the described properties and also by the diameter of the obturator. This height is preferably chosen so that the analysis of body slices having a thickness of approximately 7.5 mm is possible.

The number of photons per pulse which is received by each measuring detector or by each discrete element of the system 6 is dependent on the power of the radiation source, of the duration of the pulses, the geometry of the measuring means and of the dimensions of the detectors themselves. The number of photons received by the measuring detector, the number of is also dependent on the absorption in the tissue examined. The amplitude of the resultant electric pulses which are supplied by the photo-electric converter, i.e. the pulses I1 and I0 is dependent on the optical transmission properties of the assembly formed by the detector, light conductor and converter, and as far as the pulse I0 is concerned, on the relevant properties of the optical coupling fibre. Calculations have demonstrated that the pulses I1 and I0 have the same order of magnitude when the maximum absorption coefficient in the tissues examined is taken into account. The ratio I1/I0, in the absence of any absorbing medium, is controlled by adaptation of the penetration depth of the optical fibres in the cooperating light conductor for each photo-electric converter.

The above description of an embodiment in accordance with the invention does not constitute a limitation of the scope of the invention. As far as the method and the means are concerned, any alternative thereof which leads to the formation of a reference pulse for each absorption line which is determined in the plane of the analysis field in order to compensate for deviations and lack of homogeneity of the elements of the measuring means of the apparatus is covered by the invention.

What is claimed is:

1. Apparatus for measurement of radiation absorption in an analysis plane comprising:
   a plurality of scintillation detectors disposed in said analysis plane;
   a like plurality of scintillation elements disposed in a reference plane which is not coplanar with said analysis plane;
   radiation source means which function to project radiation along a plurality of reference lines, in said reference plane, to said scintillation elements and along a plurality of analysis lines, each of which coincide with a projection of a corresponding reference line in said analysis plane, to said scintillation detectors;
   each of said scintillation detectors including a light conductor which transmits light produced in said detector to an associated photo electric converter;
   each of said scintillation elements including an optical fibre disposed to transmit light produced in said element to the light conductor of the detector which is disposed on the corresponding analysis line; and
   obturator means which alternately interrupts said projection of radiation in said analysis plane and said reference plane.

2. Apparatus of claim 1 further including means for adjusting the optical coupling between said fibers and said conductors.

3. Apparatus of claim 2 wherein said means for adjusting includes a coupling sleeve and a micro-screw which adjustably blocks light transmission through said sleeve.

4. Apparatus of claim 1 wherein said obturator means include a slotted shield which periodically shields radiation from said reference plane and from said analysis plane.

5. An apparatus as claimed in claim 4 wherein the obturator means comprises a cylindrical lead sleeve which is disposed coaxially around the radiation source means and which rotates about its longitudinal axis, the sleeve being perforated with two parallel series of aligned slots of the same length which are regularly distributed over the circumference of the sleeve, the slots of one of the series being shifted relative to the slots of the other series over a distance equal to half the pitch of the slots of a series and disposed so that during the rotary movement of the sleeve said slots alternately intersect the analysis plane and the reference plane.

6. An apparatus as claimed in claim 5, in which the radiation source means is an X-ray tube which operates in a pulsed mode, the scintillation detectors subtend an angle of 30° at said tube each series of slots in the shield comprises five slots, each having a length of 36°, the said slots being distributed with a pitch of 72°, the shield being rotatable at a rotary speed of from 3 to 5 revolutions per second the radiation source means further comprising means for actuation of the X-ray tube with pulses having a frequency of from 30 to 50 pulses per second and a duration of from 3 ms to 1 ms.

7. In a method for determining radiation absorption in elemental areas of an analysis plane of the type wherein radiation is projected from a source along analysis lines to a plurality of scintillation detectors disposed in said analysis plane, radiation is projected along one or more reference lines to reference elements, and signals from said reference elements and said detectors are combined to compensate for inhomogeneity and deviations in measuring apparatus the improvement wherein:
   the reference lines are disposed in a plane which is not coplanar with the analysis plane;
   the reference elements are scintillation elements;
   the number of reference elements equals the number of detectors;
   the projections of the reference lines in the analysis plane coincide with the analysis lines;
   light output from each of said reference elements is adjustably coupled to light output from the associated detector; and further comprising the step of alternately shielding said radiation from said reference plane and from said analysis plane.

* * * * *